(12) United States Patent
Abribat et al.

(10) Patent No.: US 6,716,443 B1
(45) Date of Patent: Apr. 6, 2004

(54) PIT EMULSIONS

(75) Inventors: Benoit Abribat, Dannemois (FR); Maria Da Silva Marques, Vaux le Penil (FR)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/914,431

(22) PCT Filed: Feb. 18, 2000

(86) PCT No.: PCT/EP00/01311
§ 371 (c)(1), (2), (4) Date: Dec. 18, 2001

(87) PCT Pub. No.: WO00/51427
PCT Pub. Date: Sep. 8, 2000

(30) Foreign Application Priority Data

Feb. 27, 1999 (DE) .......................................... 199 08 559

(51) Int. Cl.⁷ ............................. A01N 25/00; A01N 3/02
(52) U.S. Cl. ..................................... 424/405; 504/116.1
(58) Field of Search ............................. 504/363, 116.1; 424/405

(56) References Cited

U.S. PATENT DOCUMENTS

| | | | |
|---|---|---|---|
| 3,547,828 A | 12/1970 | Mansfield et al. | |
| 3,707,535 A | 12/1972 | Lew | |
| 3,772,269 A | 11/1973 | Lew | |
| 3,839,318 A | 10/1974 | Mansfield | |
| 4,349,669 A | 9/1982 | Klahr et al. | |
| 5,037,653 A * | 8/1991 | Dawson | ...................... 424/405 |
| 5,242,907 A | 9/1993 | Dawson | |
| 6,221,370 B1 | 4/2001 | Wadle et al. | |

FOREIGN PATENT DOCUMENTS

| | | |
|---|---|---|
| AU | 674533 | 1/1997 |
| AU | 725709 | 8/1998 |
| DE | 1 165 574 | 3/1964 |
| DE | 1 943 689 | 3/1970 |
| DE | 2 036 472 | 2/1971 |
| DE | 2 024 051 | 12/1971 |
| DE | 30 01 064 | 7/1981 |
| EP | 0 077 167 | 4/1983 |
| EP | 0392127 * | 10/1990 |
| EP | 0 589 334 | 3/1994 |
| GB | 962919 | 7/1964 |
| GB | 1 333 475 | 10/1973 |
| WO | WO 93/14630 | 8/1993 |
| WO | WO 98/09721 | 3/1998 |
| WO | WO 98/32413 | 7/1998 |

* cited by examiner

*Primary Examiner*—Alton N. Pryor
(74) *Attorney, Agent, or Firm*—John E. Drach; Steven J. Trzaska

(57) ABSTRACT

PIT emulsions containing pesticides are comprised of: (a) from about 1% to about 20% by weight of a pesticide; (b) from about 5% to about 15% by weight of a nonionic emulsifier; (c) from about 0 to about 40% of a nonpolar solvent. These emulsions exhibit improved storage stability and higher activity compared with conventional pesticide emulsions.

12 Claims, No Drawings

PIT EMULSIONS

This application is a 371 of PCT/EP00/01311 filed Feb. 18, 2000.

BACKGROUND OF THE INVENTION

This invention relates generally to pesticide formulations and more particularly to special PIT emulsions containing pesticides and selected emulsifiers.

PRIOR ART

Emulsions of oil-soluble pesticides are frequently used in agriculture to protect valuable crops against pest infestation. Unfortunately, these preparations are not sufficiently stable in storage and, in particular, do not allow either the preparation of dilute forms or the addition of water-soluble pesticides without the emulsion breaking. Another problem is that the activity of the emulsions is not always satisfactory.

Accordingly, the complex addressed by the present invention was to provide new plant protection compositions containing both solid and liquid, preferably oil-soluble pesticides which would be distinguished by higher storage stability and activity and which, in particular, could be readily diluted with water and would allow the stable incorporation of additional water-soluble pesticides.

DESCRIPTION OF THE INVENTION

The present invention relates to PIT emulsions containing
(a) pesticides and
(b) nonionic emulsifiers.

It has now surprisingly been found that emulsions which contain the pesticides together with nonionic emulsifiers, more particularly combinations of fatty alcohol ethoxylates and fatty acid partial glycerides and which have been prepared by the phase inversion temperature method (PIT emulsions) excellently satisfy the complex requirement profile. The preparations are distinguished by improved storage stability and higher activity compared with conventional emulsions. In addition, they may readily be diluted with water and, in addition, allow the subsequent incorporation of water-soluble pesticides.

Pesticides

The pesticides which form component (a) are preferably oil-soluble substances. Fungicides, herbicides, insecticides or mixtures thereof may be used. Typical examples of suitable fungicides are azoxystrobin, benalaxyl, carbendazim, chlorothalonil, cupfer, cymoxanil, cyproconazol, diphenoconazol, dinocap, epoxiconazol, fluazinam, flusilazol, flutriafol, folpel, fosetyl aluminium, kresoxim methyl, hexaconazol, mancozeb, metalaxyl, metaconazol, myclobutanil, ofurace, phentinhydroxide, prochloraz, pyremethanil, soufre, tebuconazol and tetraconazol and mixtures thereof. The herbicides may be selected from alachlor, acloniphen, acetochlor, amidosulfuron, aminotriazol, atrazin, bentazon, biphenox, bromoxyl octanoate, bromoxynil, clethodim, chlodinafop propargyl, chloridazon, chlorsulfuron, chlortoluron, clomazon, cycloxydim, desmedipham, dicamba, dicyclofop methyl, diurea, diflupheniçanil, dimithenamid, ethofumesat, fluazifop, fluazifop-p-butyl, fluorochloridon, fluroxypyr, glufonsinat, glyphosat, haloxyfop-R, ioxynil octanoate, isoproturon, isoxaben, metamitron, metazachlor, metolachlor, metsulfuron methyl, nicosulfuron, notflurazon, oryzalin, oxadiazon, oxyfluorphen, paraquat, pendimethalin, phenmedipham, phenoxyprop-p-ethyl, propaquizafop, prosulfocarb, quizalofop, sulcotrion, sulphosat, terbutylazin, triasulfuron, trichlorpyr, triflualin and triflusulfuron methyl either individually or in combination with one another. Finally, suitable insecticides are biphenthrin, carbofuran, carbosulfan, chlorpyriphos methyl, chlorpyriphos ethyl, β-cyfluthrin, λ-cyhalothrin, cyhexatin, cypermethrin, dicofol, endosulfan, τ-fluvalinat, α-methrin, δ-methrin, phenbutatin, pyrimicarb, terbuphos and tebuphenpyrad and mixtures thereof. Other suitable pesticides can be found, for example, in the Index Phytosanitaire 1998, 34th Edition (published by Association de Coordination Technique Agricole, Paris).

Nonionic Emulsifiers

Suitable emulsifiers which form component (b) are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of products of the addition of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) products of the addition of 15 to 60 moles of ethylene oxide onto castor oil and/or hydrogenated castor oil;

(6) polyol esters and, in particular, polyglycerol esters such as, for example, polyglycerol polyricinoleate or polyglycerol poly-12-hydroxystearate. Mixtures of compounds from several of these classes are also suitable;

(7) products of the addition of 2 to 15 moles of ethylene oxide onto castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) trialkyl phosphates and mono-, di- and/or tri-PEG-alkyl phosphates;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 1165574 and/or mixed esters of fatty acids containing 6 to 22 carbon atoms, methyl glucose and polyols, preferably glycerol,

(13) polyalkylene glycols and

(14) glycerol carbonate.

The addition products of ethylene oxide and/or propylene oxide with fatty alcohols, fatty acids, alkylphenols, glycerol mono- and diesters and sorbitan mono- and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{2/18}$ fatty acid monoesters and diesters of adducts of ethylene oxide with glycerol are known as refatting agents for cosmetic formulations from DE-PS 2024051.

$C_{8/18}$ alkyl mono- and oligoglycosides, their production and their use as surfactants are known, for example, from U.S. Pat. No. 3,839,318, U.S. Pat. No. 3,707,535, U.S. Pat. No. 3,547,828, DE-OS 1943689, DE-OS 2036472 and DE-A1 3001064 and from EP-A1 0 077 167. They are produced in particular by reaction of glucose or oligosaccharides with primary alcohols containing 8 to 18 C atoms. So far as the glycoside component is concerned, both monoglycosides, in which a cyclic sugar unit is attached to the fatty alcohol by a glycoside linkage, and oligomeric glycosides with a degree of oligomerization of preferably up to about 8 are suitable. The degree of oligomerization is a statistical mean value on which a homolog distribution typical of such technical products is based.

A preferred embodiment of the invention is characterized by the use of mixtures of at least two nonionic emulsifiers, more particularly (b1) fatty alcohol ethoxylates and (b2) fatty acid partial glycerides. The fatty alcohol ethoxylates (component b1) preferably correspond to formula (I):

$$R^1O(CH_2CH_2O)_nH \quad (I)$$

in which $R^1$ is a linear or branched alkyl and/or alkenyl group containing 12 to 24 and more particularly 16 to 22 carbon atoms and n is a number of 1 to 30 and more particularly 10 to 20. Typical examples are products of the addition of on average 10 to 20 moles of ethylene oxide onto cetyl alcohol, stearyl alcohol, isostearyl alcohol, cetearyl alcohol and behenyl alcohol. The fatty acid partial glycerides, i.e. monoglycerides, diglycerides and technical mixtures thereof, which may still contain small quantities of triglycerides from their production and which form component (b2), generally correspond to formula (II):

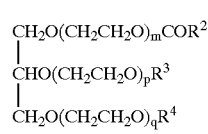

(II)

in which $R^2CO$ is a linear or branched, saturated and/or unsaturated acyl group containing 6 to 22 and preferably 12 to 18 carbon atoms, $R^3$ and $R^4$ independently of one another have the same meaning as $R^2CO$ or represent OH and the sum (m+p+q) is 0 or a number of 1 to 100 and preferably 5 to 25, with the proviso that at least one of the two substituents $R^3$ and $R^4$ represents OH. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Technical lauric acid glycerides, palmitic acid glycerides, stearic acid glycerides, isostearic acid glycerides, oleic acid glycerides, behenic acid glycerides and/or erucic acid glycerides which have a monoglyceride content of 50 to 95% by weight and preferably 60 to 90% by weight are preferably used. The ratio in which the fatty alcohol ethoxylates and fatty acid partial glycerides are used is non-critical within wide limits and may be 90:10 to 10:90, preferably 75:25 to 25:75 and more particularly 60:40 to 40:60 parts by weight.

Solvents

Particularly when pesticides solid at room temperature are to be incorporated in the emulsions, it is advisable to use nonpolar solvents. This optional component (c) may be selected, for example, from mineral oils, fatty acid lower alkyl esters such as, for example, the $C_{1-4}$ esters, i.e. methyl, ethyl, propyl and/or butyl esters, of caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Vegetable triglycerides, for example coconut oil, palm oil, palm kernel oil, sunflower oil, olive oil and the like, are also suitable.

PIT Emulsions

In one preferred embodiment, the PIT emulsions according to the invention contain (a) 1 to 20, preferably 5 to 15% by weight of pesticides, (b) 5 to 15, preferably 8 to 12% by weight of nonionic emulsifiers and (c) 0 to 40, preferably 5 to 30% by weight of solvents, with the proviso that the quantities shown add up to 100% by weight with water and optionally other typical auxiliaries and additives. The water content of the emulsions is on average 30 to 90 and more particularly 40 to 60% by weight while the droplet size is between 0.01 and 1 μm and preferably between 0.1 and 0.5 μm.

The present invention also relates to a process for the production of pesticide emulsions in which the oil-soluble pesticides are homogenized together with the nonionic emulsifiers and 40 to 60% by weight, based on the final formulation, of water and heated beyond the phase inversion temperature, the remaining water is added, the emulsion is left to cool and is then optionally diluted with more water to the required active-substance concentration and/or other water-soluble pesticides are added.

EXAMPLES

Plant protection emulsions using pesticides liquid or solid at room temperature were used. Emulsions 1 to 3 according to the invention were prepared by the PIT method while comparison emulsions C1 and C2 were prepared by the conventional hot method. The emulsions were then stored for 1 week at 20° C. and for 4 weeks at 40° C. and stability-tested; (++) means stable, (+) means slight clouding and (−) means phase separation. In addition, the prepared emulsions were diluted with water at 20° C. to an active substance content of 1% by weight and evaluated for stability in the same way. The results are set out in Table 1.

TABLE 1

| Stability of pesticide formulations | | | | | |
|---|---|---|---|---|---|
| Composition/performance | 1 | 2 | 3 | C1 | C2 |
| Pesticide (Mp. < 20° C.) | 5.0 | 5.0 | — | 5.0 | 5.0 |
| Pesticide (Mp. > 25° C.) | — | — | 5.0 | — | — |
| Cetyl stearyl alcohol + 12 EO | 12.0 | 8.0 | — | 12.0 | 8.0 |
| Behenyl alcohol + 10 EO | — | — | 8.0 | — | — |
| Glyceryl Stearate | — | 4.0 | 4.0 | — | 4.0 |
| Coconut fatty acid methyl ester | — | — | 20.0 | — | — |

TABLE 1-continued

Stability of pesticide formulations

| Composition/performance | 1 | 2 | 3 | C1 | C2 |
|---|---|---|---|---|---|
| Water | | | | to 100 | |
| Average particle size [μm] | <1 | <1 | <1 | 10–100 | 10–100 |
| Stability | | | | | |
| after storage (1 week, 20° C.) | ++ | ++ | ++ | + | + |
| after storage (4 weeks, 40° C.) | + | ++ | ++ | − | − |
| after dilution with water | + | + | + | − | − |

The PIT emulsions according to the invention were found to be stable both under temperature stress and in diluted form whereas the comparison emulsions allowed neither temperature stress nor the addition of water.

What is claimed is:

1. A composition comprising:
   (a) from about 1 to 20% by weight of an oil-soluble pesticide;
   (b) from about 5 to 15% by weight of a nonionic emulsifier containing a fatty alcohol ethoxylate and a fatty acid partial glyceride;
   (c) up to about 40% by weight of a non-polar solvent; and
   (d) remainder, to 100%, water, and wherein the composition is a PIT (Phase inversion temperature) emulsion.

2. The composition of claim 1 wherein the oil-soluble pesticide is selected from the group consisting of a fungicide, an herbicide, an insecticide, and mixtures thereof.

3. The composition of claim 1 wherein the oil-soluble pesticide is present in the composition in an amount of from about 5 to 15% by weight, based on the weight of the composition.

4. The composition of claim 1 wherein the nonionic emulsifier is present in the composition in an amount of from about 8 to 12% by weight, based on the weight of the composition.

5. The composition of claim 1 wherein the non-polar solvent is a $C_{1-4}$ alkyl ester.

6. The composition of claim 1 wherein the non-polar solvent is present in the composition in an amount of from about 5 to 30% by weight, based on the weight of the composition.

7. A process for treating crop comprising contacting said crop with a pesticide composition comprising:
   (a) from about 1 to 20% by weight of an oil-soluble pesticide;
   (b) from about 5 to 15% by weight of a nonionic emulsifier containing a fatty alcohol ethoxylate and fatty acid partial glyceride;
   (c) remainder, to 100% by weight, water and wherein the composition is a PIT emulsion.

8. The process of claim 7 wherein the oil-soluble pesticide is selected from the group consisting of a fungicide, an herbicide, an insecticide, and mixtures thereof.

9. The process of claim 7 wherein the oil-soluble pesticide is present in the composition in an amount of from about 5 to 15% by weight, based on the weight of the composition.

10. The process of claim 7 wherein the nonionic emulsifier is present in the composition in an amount of from about 8 to 12% by weight, based on the weight of the composition.

11. The process of claim 7 wherein the composition further comprises a non-polar solvent that is a $C_{1-4}$ alkyl ester.

12. The process of claim 7 wherein the composition further comprises a non-polar solvent that is present in the composition in an amount of from about 5 to 30% by weight, based on the weight of the composition.

* * * * *